(12) United States Patent
de Haan et al.

(10) Patent No.: US 8,878,012 B2
(45) Date of Patent: Nov. 4, 2014

(54) METHODS FOR IMPROVING THE YIELD OF CUCUMBER PLANTS

(75) Inventors: Anita Afke de Haan, Bleiswiji (NL); Bram Rozier, Zwijndrecht (NL); Martinus Quirinus Maria van Paassen, Delft (NL); Jeroen Sebastiaan de Vries, Den Haag (NL)

(73) Assignee: Monsanto Invest B.V., Bergschenhoek (NL)

( * ) Notice: Subject to any disclaimer, the term of this patent is extended or adjusted under 35 U.S.C. 154(b) by 9 days.

(21) Appl. No.: 12/794,863

(22) Filed: Jun. 7, 2010

(65) Prior Publication Data

US 2010/0313291 A1    Dec. 9, 2010

Related U.S. Application Data

(63) Continuation of application No. PCT/NL2008/050834, filed on Dec. 19, 2008.

(30) Foreign Application Priority Data

Dec. 20, 2007 (EP) ..................... 07150267

(51) Int. Cl.
| | |
|---|---|
| *A01H 5/10* | (2006.01) |
| *A01H 5/00* | (2006.01) |
| *A01H 4/00* | (2006.01) |
| *A01H 1/04* | (2006.01) |
| *A01H 5/08* | (2006.01) |
| *C12Q 1/68* | (2006.01) |

(52) U.S. Cl.
CPC .. *A01H 5/08* (2013.01); *A01H 1/04* (2013.01); *C12Q 1/6895* (2013.01)
USPC ............ 800/307; 800/260; 800/265; 800/266

(58) Field of Classification Search
None
See application file for complete search history.

(56) References Cited

PUBLICATIONS

Shetty et al 2002 Crop Science 42:2174-2183.*
Visscher et al 1996 Genetics 144:1923-1932.*
Bai et al 1999 Phytopathology 89:343-348.*
Horejsi, et al., "Genetic Variation in Cucumber (*Cucumis sativus* L.) as Assessed by Random Amplified Polymorphic DNA," Genetic Resources and Crop Evolution, 46: 337-350, 1999.
Fazio et al., Comparative analysis of response to phenotypic and marker-assisted selection for multiple lateral branching in cucumber (*Cucumis sativus* L.); *Theor. Appl. Genet.*; 107;875-883; 2003.
Xie et al., "Gene List 2001 for Cucumber," *Curcurbit Genetics Cooperative Report*; 110-136; 2001.
Wehner et al., "Screening the Cucumber Germplasm Collection for Combining Ability for Yield," *HortScience* 35(6):1141-1150, 2000.
USDA-GRIN listing for Cucumber accession PI 169383, 1948.

* cited by examiner

*Primary Examiner* — Brent T Page
(74) *Attorney, Agent, or Firm* — Dentons US LLP

(57) ABSTRACT

The present invention relates to a plant of a cucumber breeding line having an introgression from cucumber accession PI 169383, a representative sample of seed of which has been deposited with the NCIMB, Aberdeen, Scotland under accession number NCIMB 41532 and depositors reference PI169383, wherein said introgression is an introgression on linkage group 4 associated with increased yield of said plants, wherein said plant exhibits an increased yield relative a plant of said cucumber breeding line lacking said introgression, and wherein said increased yield refers to a higher total fruit weight per plant.

18 Claims, 5 Drawing Sheets

SEQUENCE LISTING

```
<160> NUMBER OF SEQ ID NOS: 8

<210> SEQ ID NO 1
<211> LENGTH: 83
<212> TYPE: DNA
<213> ORGANISM: Artificial Sequence
<220> FEATURE:
<223> OTHER INFORMATION: Amplified fragment length polymorphism marker

<400> SEQUENCE: 1
gactgcgtac caattcctct agtactttct tctgtttctc ttatttcctt tcctgaatat      60
aattatgtta ctcaggactc atc                                             83

<210> SEQ ID NO 2
<211> LENGTH: 225
<212> TYPE: DNA
<213> ORGANISM: Artificial Sequence
<220> FEATURE:
<223> OTHER INFORMATION: Amplified fragment length polymorphism marker

<400> SEQUENCE: 2
gactgcgtac caattcattc taaattcaaa ttccgtccta aattgttgat ttggtaagga      60
agttgtgaga attgttttgg gatgggatga gataattgtg gtaggctgta ttgctttcca     120
ttgttgtgta tgtgtatgtg atattgtatt gttgttcttt tttggttgag tttgggtgct     180 cttttttgcct cctgggttta tggttggagt tactcaggac tcatc                    225
```

```
<210> SEQ ID NO 3
<211> LENGTH: 223
<212> TYPE: DNA
<213> ORGANISM: Artificial Sequence
<220> FEATURE:
<223> OTHER INFORMATION: Amplified fragment length polymorphism marker

<400> SEQUENCE: 3
gactgcgtac caattcatct gtttgtattg acttctcatt attcatgtag acaaaaagag      60
acaaatatag agagttcaag tgtgtgtgta tgtgtgcata aagcactaga tagggttgag     120
gtttagggca catcaaacca atatatatac aaccactcct gaatattcgg tgcaagtcca     180
cgtactttac ttttttttac ttttgagtta ctcaggactc atc                      223

<210> SEQ ID NO 4
<211> LENGTH: 181
<212> TYPE: DNA
<213> ORGANISM: Artificial Sequence
<220> FEATURE:
<223> OTHER INFORMATION: Amplified fragment length polymorphism marker

<400> SEQUENCE: 4
gactgcgtac caattcatta cacgacatgt agatctaatt gctgaacaaa aaaaaaaaa      60 aaaaagcaat tctgcaagaa ctccagaaac aaaattaggg gtaggctttt ttgtctatag    120
aaaagtagtt ggtgtgacag aaccattgtt tgcaataggc tggagttact caggactcat    180
c                                                                    181

<210> SEQ ID NO 5
<211> LENGTH: 198
<212> TYPE: DNA
<213> ORGANISM: Artificial Sequence
<220> FEATURE:
<223> OTHER INFORMATION: Amplified fragment length polymorphism marker
<220> FEATURE:
<221> NAME/KEY: misc_feature
<222> LOCATION: (2)..(2)
<223> OTHER INFORMATION: wherein N is G, A, T or C

<400> SEQUENCE: 5
gnctgcggac caattcaact gtaaactagg aaactctaat gatctagttt tagttgatat      60
tgaacaatat caacgtctcg tgggtaaatt gatttactta tcccatactt gtcctgatat    120
ttcctttgct gtgagtgttg tcacccagtt tatgcaggct ccttatgaga aacacatgga    180
agttactcag gactcatc                                                  198

<210> SEQ ID NO 6
<211> LENGTH: 216
<212> TYPE: DNA
<213> ORGANISM: Artificial Sequence
<220> FEATURE:
<223> OTHER INFORMATION: Amplified fragment length polymorphism marker

<400> SEQUENCE: 6
gacgtaccaa ttcctgcaga tagattatgc cgcttagaat gtcatgagtg accgagatgg      60
tagattcatt ggcacatttt ggactaaact attcactttc tcaggaacaa gtctgaatgt    120
gtcctcaagt taccatcctc aaatagacgg tcagatcgaa cgattcaaat gtatgctcga    180
ataatatttg cgccattttg ttactcagga ctcatc                              216

<210> SEQ ID NO 7
<211> LENGTH: 223
```

```
<212> TYPE: DNA
<213> ORGANISM: Artificial Sequence
<220> FEATURE:
<223> OTHER INFORMATION: Amplified fragment length polymorphism marker

<400> SEQUENCE: 7
gactgcgtac caattcagag acgtggtttt ataaaaaaga gaaaaaaagc tattagggac        60
atagctggca aatataagat gatcagtcat attgctcata ctcatagagt catagcaagt       120
ctaaggatta ctttgagatt gctttattta caaaatgttg gttagagaga catcaatttt       180
tttaggaagc caatctctag aactacgtta ctcaggactc atc                         223

<210> SEQ ID NO 8
<211> LENGTH: 76
<212> TYPE: DNA
<213> ORGANISM: Artificial Sequence
<220> FEATURE:
<223> OTHER INFORMATION: Amplified fragment length polymorphism marker

<400> SEQUENCE: 8
gactgcgtac caattcggtg gttagattgt atttctacaa tctctttgtc gttgggttgg        60
ttactcagga ctcatc                                                       76
```

METHODS FOR IMPROVING THE YIELD OF CUCUMBER PLANTS

RELATED APPLICATIONS

This application is a continuation of PCT application number PCT/NL2008/050834 designating the United States and filed Dec. 19, 2008; which claims the benefit of EP patent application number 07150267.8 and filed Dec. 20, 2007 both of which are hereby incorporated by reference in their entireties.

FIELD OF THE INVENTION

The present invention relates to plant breeding, more in particular, the present invention relates to methods for improving the yield of cucumber plants. The invention further relates to cucumber plants having improved crop yields and the seeds from such plants.

BACKGROUND OF THE INVENTION

Cucumber (*Cucumis sativus*) is a major vegetable crop worldwide and among the most important crop species in the Cucurbitaceae family. They are eaten as a vegetable, either raw, cooked, or made into pickled cucumbers. The more than 100 varieties produce oblong fruits ranging in size from small picklers to large slicers and from can range in color from yellow or brown to a dark green for the cultivated varieties. Modern cultivated cucumbers are typically seedless and while they are generally considered less nutritious than most other fruits, the fresh cucumber is a good source of vitamins A, B1, B5, B6, B9, C, and K, and minerals. Most greenhouse varieties produce fruit without pollination and are gynoecious with respect to flowering, (i.e. produce only female flowers).

The yield potential of greenhouse cucumbers is high since at the base of every leaf one or more flowers are produced that will develop into fruits. Fruits are harvested at market maturity which requires a uniform diameter throughout the length of the fruits. The harvest or marketable stage is generally reached 12 to 15 days after opening of the flower. Compared with many crops, cucumber reaches harvest stage rapidly. In fact, many varieties of cucumber are ready to harvest after 50-60 days from seeding. Cucumber vines bear fruit in abundance and when harvested on a frequent basis (every 2 to 3 days) and in particular before the fruits reach full maturity, the setting of new flowers is encouraged and the harvest period may have a duration of 10 to 12 weeks. A two-crop rotation is most common, although three-crop rotations are also employed.

Cucumber yields depend mainly on the length of the harvest period, the spacing of individual plants, the pruning practice employed, the available light, the prevailing temperature, the particular variety, and good nutritional and pest management. The number of plants to be grown in a given area of greenhouse is determined by light conditions and by the method of training of the plants. While leaf overlapping and shading by adjacent plants must be avoided, summer light conditions will allow a higher planting density than winter conditions. The plants may be trained vertically or in the shape of an umbrella. Planting density is generally 2 plants per m². Considering these variables, an average plant may yield 10-50 cucumbers per plant per harvest period. During mid-harvest on an umbrella-trained crop yields may range from 0.5-1.5 kg of fruit per plant per week.

It is a challenge to modern cucumber breeders to improve the yield of current cucumber hybrids, in particular the yield expressed as kg of fruit/plant. Conventional breeding methods have thus far not resulted in significant improvements of crop yields. For instance, the average yield of pickling cucumber in the United States has almost doubled in the period form 1960-1980 due to improved cultural practices, and selection for yield and disease resistance. However, in the last two decades, no significant improvements have been achieved. One of several routes can be taken to solve this problem.

One method for improving yield is based on further improving nutrient and pest management. However, in modern controlled production environments, these parameters have usually been optimized.

Other methods involve improving the breeding lines. Plant breeders and in particular seed companies employ elite breeding lines, generally referred to as "elite lines" to provide a constant quality product. The elite lines are the result of many years of inbreeding and combine multiple superior characteristics such as high yield, fruit quality, and resistance to pests, disease, or abiotic stress. The average yield of these elite lines is generally much higher than the original wild (landrace) accessions from which many of the modern cucumbers are descendants. The elite lines are used directly as crop plant or can be used to produce so-called F1 or single-cross hybrids, produced by a cross between two (homozygous or inbred) elite lines. The F1 hybrids thus combine the genetic properties of the two parents into a single plant. An add-on benefit of hybrids is that they express hybrid vigour or heterosis, the poorly understood phenomenon that hybrid plants grow better than either (inbred) parent and show higher yields.

Backcross or pedigree selection is one method by which breeders add desirable agronomic traits to their elite breeding lines. The method involves crossing the breeding line with a line that expresses the desirable trait followed by backcrossing offspring plants expressing the trait to the recurrent parent. As a result, the selection of an individual as a parent in a breeding program is based on the performance of its forebears. Such methods are most effective in breeding for qualitatively-inherited traits, i.e traits which are scored positive or negative. However, many traits of interest to growers, such as yield, earliness and quality, are quantitatively inherited and have low heritability. In the absence of a suitable source of the trait, no improvements can be made.

Recurrent selection is an alternative breeding method for improving breeding lines and involves systematic testing and selection of desirable progeny followed by recombination of the selected individuals to form a new population. Recurrent selection has proven effective for improving quantitative traits with low heritability, such as yield, in cucumber. Recurrent selection however does not increase the genetic basis underlying the various traits in a breeding program, and its potential is therefore limited. Over time, only marginal improvement have been realized.

There is a need for an additional method to improve the yield of cucumber. It is an aim of the present invention to provide methods for producing cucumber plants having improved crop yield. It is another aim of the present invention to provide cultivated cucumber plants having improved crop yield.

SUMMARY OF THE INVENTION

The present inventors have discovered that a particular wild cucumber accession may be used in methods for improving the yield of cultivated varieties of cucumber. This discovery came about when investigating an introgression line (IL) library that was developed by introgressing chromosomal segments from the wild cucumber (*Cucumus sativus*) accession PI 169383 (see FIG. 2) as donor plant into the corresponding chromosomal positions in plants of one of the parents of a commercial cucumber hybrid (also *C. sativus*) as the recipient. Phenotyping of the developed IL-library, showed a remarkable increase in the yield of some of the introgression lines. Detailed mapping studies revealed that the improved yield characteristics were associated with three segments from PI 169383 in linkage group 4. The introgression of these segments in the corresponding chromosome of a cultivated cucumber plant resulted in an increase in yield in offspring of said cultivated cucumber plant. The introgression segments could be characterized as Quantitative Trait Loci (QTLs), and the location of these QTLs in the genome of cucumber was defined by 7 AFLP-markers. Further phenotyping of the introgressions was performed in heterozygous situations and in hybrid situations. The results are presented in the Examples described below.

Based on this finding, the inventors provide a novel genetic basis for desirable phenotypic characteristics related to improved yield. This genetic basis is present in the wild cucumber (*Cucumus sativus*) accession PI 169383.

Although the genes or causal sequences underlying the phenotypic property of increased yield have not (yet) been identified, the genomic location of the genes or causal sequences (i.e. the locus) has been determined. This facilitates the breeding process wherein the genes or regulatory sequences are introduced into a desired cucumber breeding line.

In a first aspect, the present invention provides a plant of a cucumber breeding line having an introgression from cucumber accession PI 169383, wherein said introgression is an introgression on linkage group 3 and/or 4 associated with increased yield of said plants, and wherein said plant exhibits an increased yield relative a plant of said cucumber breeding line lacking said introgression. Preferably said increased yield refers to a higher total fruit weight per plant.

As an example, the present inventors crossed a plant from cucumber accession PI 169383 as a donor line of the introgression, with plants of cucumber line Pyr42, a representative sample of seed of which has been deposited with the NCIMB, Aberdeen, Scotland under accession number NCIMB 41594 and depositors reference Pyr42. The resulting offspring was backcrossed using Pyr42 as the recurrent parent. It was found that the plants comprising the introgression which is herein referred to as the yield-improving QTL provided the plant with an increased yield relative a plant of line Pyr42 lacking said introgression.

In aspects of the present invention the increase in yield is preferably such that the total fruit weight per plant is increased by at least 3-5%, more preferably by at least 10%, relative to a plant of said cucumber breeding line lacking said introgression.

When referring to total fruit weight per plant, reference is preferably meant to be made to the total weight of marketable fruits produced per plant per harvestable period. Cucumbers are harvested at market weight, and a plant producing a high number of fruits at market weight is advantageous over a plant producing a high number of fruits below market weight. The weight of a marketable fruit depends on the type of cucumber. Slicers and Beit Alpha's have higher weights of marketable fruits than picklers. Preferably the yield increase as referred to in the present invention refers to yield increase for slicers, Beit Alpha's and long cucumbers (Long Dutch or European greenhouse cucumber), most preferably for long cucumbers. Preferred cucumber fruits of the invention have a length of between 26, most preferably 27, 28, 29, 30, 31, 32, 33, 34, 35, 36, 37, 38, 39, 40, 41, 42, 43, 44, or 45 cm. The length/diameter ratio of the fruits of plants of the present invention is preferably 4, 5, 6, 7, 8, 9 or more, such as 25. Weight of a marketable fruit of the plants of the invention are preferably between 150-900 g, more preferably 200-800 g, still more preferably 250-600 g. The typical weight of a marketable fruit may strongly depend on the type of cucumber. For an American slicer, the weight of a marketable fruit is about 150-230 g, whereas for a European greenhouse cucumber, the weight of a marketable fruit is typically about 300-700 g. For Beit Alpha the weight of a marketable fruit is about 90-200 gr. Typically, Beit Alpha cucumbers are 12-18 cm in length. For pickling types, the weight of a marketable fruit is about 80-110 gr. Typically, pickling cucumbers are 9-12 cm in length. These fruit weights are attained under commercial growth conditions, wherein plants are pruned and harvested for optimal performance. Under such conditions, the weight of marketable fruits as contemplated herein is reached.

In a preferred embodiment, a plant of a cucumber breeding line according to the invention essentially has acquired a specific introgression from cucumber accession PI 169383, wherein said introgression is located on linkage group 3 and/or 4 comprising the QTL associated with increased yield. Although the plant receiving the introgression may have obtained other introgressions from the same donor, it is preferred that the majority of the recipient genome is unaltered, so that the phenotype of the breeding line plant is essentially conserved. This cannot be attained by simply crossing a plant of line PI 169383 with a plant of a cucumber breeding line, since that would not result in an introgression of the yield QTL as defined herein, but merely in a hybrid having one set of chromosomes from PI 169383 and the other from the plant of said cucumber breeding line. Instead, the segment on linkage group 3 and/or 4 associated with an increase in yield in PI 169383 may be introgressed into the genome of a plant of a cucumber breeding line by crossing said plants followed by one or more steps of selfing and/or backcrossing (to another plant of said cucumber breeding line as the recurrent parent) and selecting plants from the progeny population of said selfing and/or backcrossing having the introgression by using marker-assisted selection.

In a preferred embodiment said introgression on linkage group 3 and/or 4 comprises:
  at least one segment on linkage group 4 selected from the group consisting of:
    i) the segment associated with AFLP markers E12/M24-F-063-P2; E11/M62-F-200-P1;
    ii) the segment associated with AFLP markers E12/M24-F-177-P2; E12/M24F-176-P1; E25/M13-F-128-P2;
    iii) the segment associated with AFLP marker E21/M16-F-080-P2; and/or
  a chromosome substitution of linkage group 3.

The genetic distances indicate in centimorgan in FIG. 1 are indicative and were determined for the populations under study. These values may be different for other populations. Therefore, the markers themselves provide the best definition of the location of the QTL. The figure also indicates which markers do not define the segments associated with increased yield.

The plant of a cucumber breeding line having the said introgression may be produced into an elite line by consecutive steps of backcrossing to the recurrent parent in order to make the line increasingly pure or inbred. Thus, the present invention also provides elite lines having increased yield. Said elite lines have an introgression from cucumber accession PI 169383, wherein said introgression is an introgression on linkage group 3 and/or 4 associated with an increase in yield.

In another aspect, the present invention provides a cucumber seed produced by crossing or selfing the plant of the cucumber breeding line of the invention. Preferably said seed is a hybrid seed, in particular an F1 hybrid seed. Such hybrid seeds may for instance be produced by crossing two elite lines of the invention.

In another aspect, the present invention provides a cucumber plant produced by growing the seed of the invention. In another aspect, the present invention provides a plant part of this plant. Preferably said plant part is a cucumber fruit or seed.

In another aspect, the present invention provides a method for producing a hybrid cucumber seed comprising crossing the plant of a breeding line (preferably an elite line) of cucumber of the invention having an introgression from cucumber accession PI 169383 as defined above with an other cucumber plant and harvesting the resultant hybrid cucumber seed. In a preferred embodiment, said other cucumber plant is a plant of a breeding line of cucumber, more preferably a plant of a (different) elite line. Said other cucumber plant is preferably a plant having the introgression from cucumber accession PI 169383 as defined above.

In another aspect, the present invention provides a hybrid cucumber seed produced by the method of the invention. This hybrid cucumber seed is characterized in that it contains the introgression from cucumber accession PI 169383 as defined above in the genomic background of a breeding line (preferably an elite line) of cucumber, in heterozygous or homozygous form, wherein said introgression is preferably defined by the AFLP markers as described above. This hybrid seed, when allowed to germinate, will provide a hybrid cucumber plant having all the characteristics of a normal cross between said plant of a breeding line (preferably an elite line) of cucumber of the invention with an other cucumber plant as referred to above (i.e. it will produce marketable fruits of significant commercial value), but at a higher yield. Both the homozygous and heterozygous plants are part of the present invention since the yield characteristic is an additive feature, also expressed in heterozygous plants.

In another aspect, the present invention provides a hybrid cucumber plant, produced by growing the hybrid cucumber seed of the invention.

In another aspect, the present invention provides a plant part of the hybrid cucumber plant of the invention.

In another aspect, the present invention provides a method for improving the yield of a plant of a cucumber breeding line, said method comprising the steps of:
a) crossing a plant of a cucumber breeding line with a plant of cucumber line PI 169383;
b) selecting a progeny cucumber plant resulting from said crossing having an introgression from cucumber accession PI 169383 on linkage group 4 associated with increased yield;
c) selfing and/or backcrossing said progeny cucumber plant selected in step (b) using said cucumber breeding line as a recurrent parent;
d) selecting a progeny cucumber plant resulting from the selfing or backcrossing in step (c) having an introgression from cucumber accession PI 169383 on linkage group 4 associated with increased yield
e) repeating said steps of selfing and/or backcrossing and selection of steps (c) and (d) to provide a plant of a cucumber breeding line essentially homozygous for said introgression, wherein at least one selection as performed in steps (b) or (d) is performed by marker-assisted selection.

In a preferred embodiment of such a method, said cucumber breeding line is an elite line.

In another aspect, the present invention provides a method for improving the yield of an F1 cucumber hybrid, said method comprising the steps of:
a) crossing a plant of at least a first parental line of said F1 cucumber hybrid with a plant of cucumber line PI 169383;
b) selecting a progeny cucumber plant resulting from said crossing having an introgression from cucumber accession PI 169383 on linkage group 4 associated with increased yield;
c) selfing and/or backcrossing said progeny cucumber plant selected in step (b) using said parental line of said F1 cucumber hybrid as a recurrent parent;
d) selecting a progeny cucumber plant resulting from the selfing or backcrossing in step (c) having an introgression from cucumber accession PI 169383 on linkage group 4 associated with increased yield;
e) repeating said steps of selfing and/or backcrossing and selection of steps (c) and (d) to provide a parental line of said F1 cucumber hybrid essentially homozygous for said introgression;
f) using said parental line obtained in step (e) as a parental line for the production of an F1 hybrid having increased yield,
wherein at least one selection as performed in steps (b) or (d) is performed by marker-assisted selection.

In preferred embodiments of the above methods, the marker-assisted selection procedure comprises the selection for AFLP markers E12/M24-F-063-P2; E11/M62-F-200-P1; E12/M24-F-177-P2; E12/M24-F-176-P1; E25/M13-F-128-P2 and E21/M16-F-080-P2.

In yet another aspect, the present invention provides a cucumber breeding line or an F1 cucumber hybrid obtained by a method according to the invention.

In yet another aspect, the present invention provides an isolated nucleic acid sequence comprising a QTL associated with increased yield in cucumber, wherein said QTL is defined by:
i) the segment on linkage group 4 associated with AFLP markers E12/M24-F-063-P2; E11/M62-F-200-P1;
ii) the segment on linkage group 4 associated with AFLP markers E12/M24-F-177-P2; E12/M24-F-176-P1; E25/M13-F-128-P2;
iii) the segment on linkage group 4 associated with AFLP marker E21/M16-F-080-P2.

In yet another aspect, the present invention provides the use of a genetic marker selected from the group consisting of AFLP markers E12/M24-F-063-P2; E11/M62-F-200-P1; E12/M24-F-177-P2; E12/M24-F-176-P1; E25/M13-F-128-P2 and E21/M16-F-080-P2, for the detection of a QTL associated with increased yield in cucumber plants.

In yet another aspect, the present invention provides a method for selecting a cucumber plant or part thereof, including a seed, comprising the steps of:
(a) providing a progeny cucumber plant or part thereof by crossing a plant of a cucumber breeding line with a plant of cucumber line PI 169383, obtaining seed from said cross and growing said seed into a progeny plant;
(b) testing said progeny cucumber plant or part thereof for a the presence of an introgression segment from cucumber accession PI 169383, a representative sample of seed of which has been deposited with the NCIMB, Aberdeen, Scotland under accession number NCIMB 41532 and depositors reference PI169383, wherein said introgression is an introgression on linkage group 4 associated with increased yield of said plants;

(c) selecting said progeny cucumber plant or part thereof based on the information derived from said testing; and (d) optionally using said information for further breeding considerations.

DETAILED DESCRIPTION OF THE INVENTION

Definitions

Figure 1:
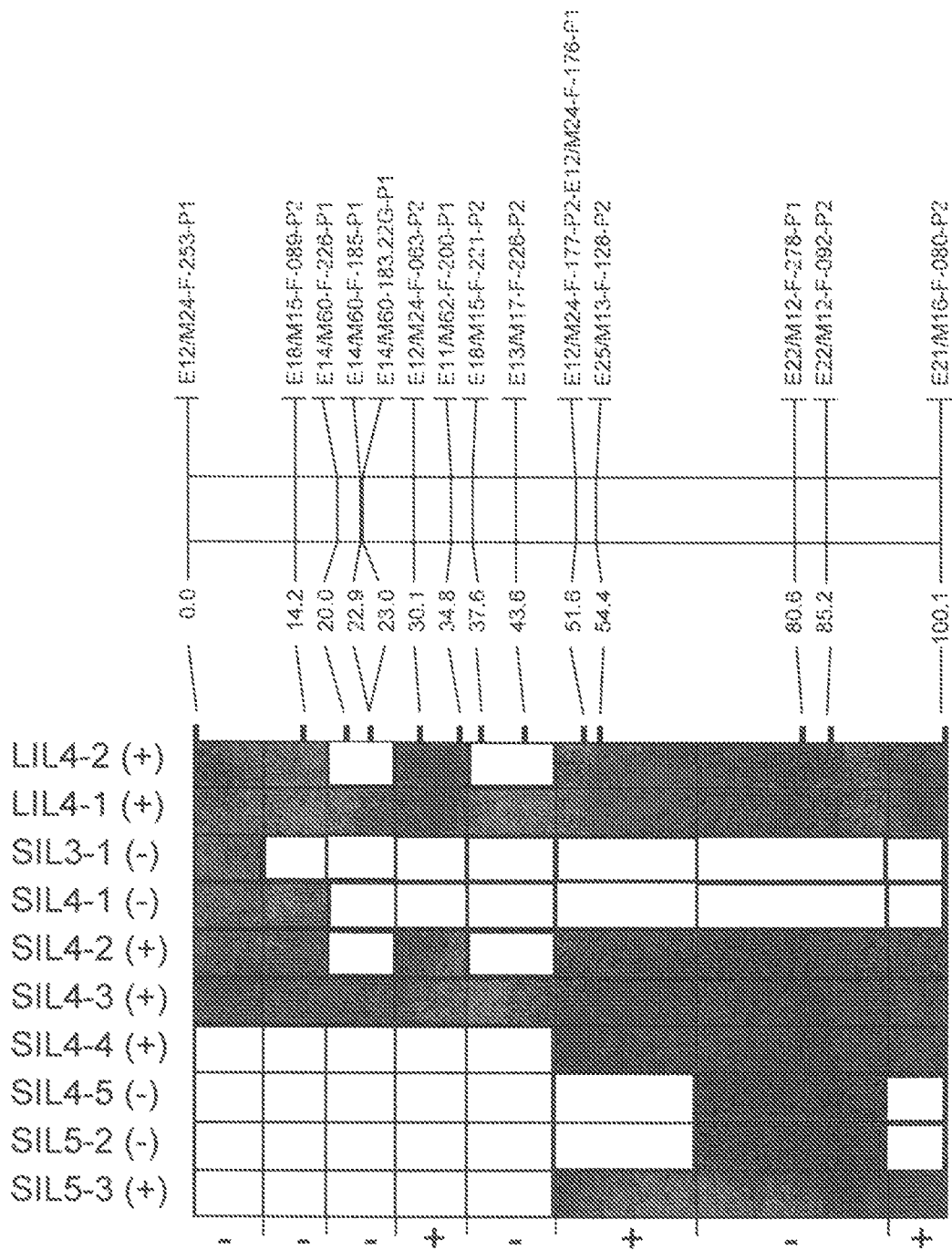
FIG. 1 presents a genetic map of linkage group 4 (total length 100.1 cM), providing the identity of the markers and their respective position relative to each other, and also indicates the association with introgression segments (indicated on the left) that have (+) or have not (−) an effect on the yield (compare Table 2). The three segments on linkage group 4 that were found to have an effect on the yield are indicated below the diagram by a "+".

The term "cucumber" as used herein refers to the species *Cucumis sativus* L., including *Cucumis sativus* L. var. *hardwickii* (Royle) or weedy cucumber, *Cucumis sativus* L. var. *sativus* or cultivated cucumber, *Cucumis sativus* L. var. *sativus* (Chinese Group) or netted yellow cucumber, *Cucumis sativus* L. (Gherkin Group) or pickling cucumber, *Cucumis sativus* L. var. *sativus* (Indian Group) or White-striped cucumber, *Cucumis sativus* L. var. *sativus* (Japanese Group) or Japanese cucumber, *Cucumis sativus* L. var. *sativus* (Lebanese Group) or Lebanese cucumber, *Cucumis sativus* L. var. *sativus* (Russian Group) or Russian cucumber, *Cucumis sativus* L. var. *sativus* (Seedless Group) or Seedless cucumber, *Cucumis sativus* L. var. *sativus* (Standard Group) or common cucumber/greenhouse cucumber, *Cucumis sativus* L. var. *sikkimensis* Hook. f. or brown netted cucumber, and *Cucumis sativus* L. var. *xishuangbannanesis* fined or Xishuangbanna gourd. Botanically speaking the name *Cucumis sativus* L. refers to the wild species but in the seed and vegetable trades it is used as a synonym for any longer botanical name that taxonomists may apply to the cultivated varieties. "*C. sativus* L. var. *sativus*" is generally used, based on the almost 1500 accessions entered in the USDA GRIN Database. However, this name may change in the future because taxonomists disapprove of domesticated plants referred to as botanical varieties "var.". The term "cucumber" includes reference to (American and European) pickling, (American and European) slicing, European greenhouse (parthenocarpic), middle-eastern (Beit Alpha types), and oriental trellis (Burpless) cucumbers. The terms European, American, middle-eastern or oriental are not intended to limit the regional origin or production regions of the cucumber of the invention, but merely refer to commonly used referrals to market types in the art of cucumber breeding.

*Cucumis sativus* var. *sativus* accession PI 169383 is maintained by the North Central Regional Plant Introduction Station at Ames, Iowa, USA (USDA, ARS, NCRPIS, Iowa State University, Regional Plant Introduction Station), and seed of this accession is freely available for distribution. This accession has the biological status "wild". This botanical variety was first collected in Istanbul, Turkey. Its fruits have a typical yellow color when ripe and are of limited commercial value, based on the low yield and general requirement for green fruits. When referring to plants of the present invention, no reference is intended to Cucumber accession PI 169383, and such plants are therefore disclaimed from the present invention. More information on this accession is available from the Online Database of the Germplasm Resources Information Network (GRIN), USDA, ARS, National Genetic Resources Program. National Germplasm Resources Laboratory, Beltsville, Md. (world wide website ars-grin.gov) (8 Aug. 2007)). A representative sample of seed of cucumber accession PI 169383 has been deposited with the NCIMB, Aberdeen, Scotland by the applicant/assignee of the present application on 17 Dec. 2007, under accession number NCIMB 41532 and depositors reference PI169383.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

As used herein, the term "hybrid" means any offspring of a cross between two genetically unlike individuals, more preferably the term refers to the cross between two (elite) breeding lines which will not reproduce true to the parent from seed. Hybrid cucumbers of the present invention preferably exhibit strong femaleness.

The term "breeding line", as used herein, refers to a line of a cultivated cucumber having commercially valuable or agronomically desirable characteristics, as opposed to wild varieties or landraces. In particular, the breeding line is characterized by having an excellent fruit quality (straight, cylindrical, and blocky shape and uniform dark green color). The term includes reference to elite breeding line or elite line, which represents an essentially homozygous, usually inbred, line of plants used to produce F1 hybrids. The breeding lines of the present invention preferably exhibit powdery mildew resistance.

As used herein, the term "yield" refers to fruit yield (cucumbers) and may refer to production expressed as total fruit weight (in kg) per $m^2$ of field per harvest period, as total fruit weight (in kg) per plant per harvest period, and combinations thereof. The term "harvest period" refers to the period between the production of the first marketable fruits and the end of the productive phase when rejuvenation of the crop is required and generally spans a period of about 12 weeks for greenhouse cucumber.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to QTLs, i.e. genomic regions that may comprise one or more genes, but also regulatory sequences, it is in some instances more accurate to refer to "haplotype" (i.e. an allele of a chromosomal segment) in stead of "allele", however, in those instances, the term "allele" should be understood to comprise the term "haplotype".

A "gene" is defined herein as a hereditary unit (often indicated by a sequence of DNA) that occupies a specific location on a chromosome and that contains the genetic instruction for a particular phenotypic characteristics or trait in a plant. A QTL (quantitative trait locus) is a hereditary unit (often indicated by one or more molecular genomic markers) that occupies a specific location on a chromosome and that contains the genetic instruction for a particular phenotypic characteristics or trait in a plant. In contrast to a gene, the exact boundaries of a QTL are not known, but can be found without undue burden by persons skilled in the art by using fine mapping techniques well known in the art of genetic mapping and subsequent DNA sequencing routines. The QTL encodes at least one gene the expression of which, alone or in combination with other genes, results in the phenotypic trait being expressed, or encodes at least one regulatory region that controls the expression of at least one gene the expression of which, alone or in combination with other genes, results in the phenotypic trait being expressed. A QTL may be defined by indicating its genetic location in the genome of the donor of the introgression that contains the QTL using one or more molecular genomic markers. One or more markers, in turn, indicate a specific locus. Distances between loci are usually measured by frequency of crossing-over between loci on the same chromosome. The further apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL. Markers that define the QTL may be markers that are linked to the QTL or markers that are in linkage disequilibrium with the QTL.

As used herein, the term "molecular genomic marker" or short "marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A "molecular marker linked to a QTL" as defined herein may thus refer to SNPs, insertion mutations as well as more usual AFLP markers or any other type of marker used in the field. In the context of AFLP markers named herein the markers indicate a cucumber-specific DNA sequence flanked by two AFLP-primers, which primers consist of "core primers" E and M, corresponding with the restriction sites of the restriction enzymes EcoRI and MseI, (Vos et al., 1995, *Nucleic Acids Res.* 23: 4407-4414; Bai et al. 2003, *Mol. plant microbe interactions* 16:169-176) followed by 2 or 3 extra selective bases as indicated, each followed by a two-digit code identifying the selective nucleotides by which the "core primer" is extended (11: AA; 12: AC; 13: AG; 14: AT; 15: CA; 16: CC; 17: CG; 18: CT; 21: GG; 22: GT; 24: TC; 25: TG; 60: CTC; 62: CTT). E12/M24-F-063-P2 thus represents a marker obtained by using amplification primers EcoRI+AC and MseI+TC to produce a fragment having a total length of 63 bp. The length of the fragment may depend on the method used to detect the fragment, and is an approximation of its true length, plus or minus a few bases. In defining a marker as provided herein reference should be made to the position on the chromosome of that marker relative to other markers in a linkage map. Thus, marker E12/M24-F-063-P2 is defined both by the sequence of its primers, as well as by its length as an amplification product, and by its position relative to E11/M62-F-200-P1 and/or E12/M24-F-177-P2 or, as provided herein, by its position relative to other markers as depicted with corresponding distance in cM in FIG. 1.

A "locus" is defined herein as the position that a given gene occupies on a chromosome of a given plant species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

The term "introgression line", abbreviated IL, as used herein refers to a line that harbours defined chromosome segments (preferably a single defined chromosome segment, depending on the marker-resolution) that originate from the donor parent in an otherwise uniform background, and typically contains more than 95% of the recipient genome (usually the genome of a breeding line which is used as the recipient and recurrent parent). ILs facilitate the identification of QTLs because phenotypic variation between different ILs in an IL library (together covering the entire genome of a donor) and the recurrent parent is directly associated with the introgressed segment. Introgression lines are typically homozygous.

As used herein, the term "pure inbred" or "inbred" refers to a substantially homozygous plant or plant line obtained by repeated selfings.

A "recombination event" refers to a meiotic crossing-over event.

As used herein, the term "introgression" refers to a genomic segment that has moved from one individual, species, variety or cultivar into the genome of another individual, species, variety or cultivar, by crossing those individuals, species, varieties or cultivars.

As used herein, the terms "introgressing", "introgress" and "introgressed" refer to both a natural and artificial process whereby individual genes or entire traits are moved from one individual, species, variety or cultivar into the genome of another species, variety or cultivar, by crossing those species, varieties or cultivars. In plant breeding, the process usually involves selfing or backcrossing to the recurrent parent to provide for an increasingly homozygous plant having essentially the characteristics of the recurrent parent in addition to the introgressed gene or trait.

The term "backcross" refers to the process wherein the plant resulting from a cross between two parental lines is crossed with one of its parental lines, wherein the parental line used in the backcross is referred to as the recurrent parent. Repeated backcrossing results in the genome becoming more and more homozygous or inbred.

The term "selfing" refers to the process of self-fertilization wherein an individual is pollinated or fertilized with its own pollen.

"Genetic engineering", "transformation" and "genetic modification" are all used herein as synonyms for the transfer of isolated and cloned genes into the DNA, usually the chromosomal DNA or genome, of another organism.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

As used herein, the term "plant part" indicates a part of the cucumber plant, including single cells and cell tissues such as plant cells that are intact in plants, cell clumps and tissue cultures from which cucumber plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like. Plant parts of the invention may be used in fresh and/or processed form in aspects of the invention.

As used herein, the term "population" means a genetically heterogeneous collection of plants sharing a common genetic derivation.

As used herein, the term "variety" refers to a group of similar plants that by structural or genetic features and/or performance can be distinguished from other varieties within the same species.

The term "cultivar" (for cultivated variety) is used herein to denote a variety that is not normally found in nature but that has been cultivated by humans, i.e. having a biological status other than a "wild" status, which "wild" status indicates the original non-cultivated, or natural state of a plant or accession. The term "cultivar" includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar.

The term "elite background" is used herein to indicate that the genetic background of a QTL or introgression is that of a breeding line. In the present instance the natural background is the genetic background of Cucumber accession PI 169383. A method that involves the transfer of DNA comprising the QTL from Linkage group (chromosome) 4 of Cucumber accession PI 169383 to the same position on chromosome 4 of a plant of a breeding line will result in that QTL not being in its natural genetic background, but in an elite background. The term both includes heterozygous as well as homozygous situations.

DESCRIPTION OF THE PREFERRED EMBODIMENTS

Producing Plants with Higher Yields

The effect of the introgressions as identified herein is high yield in fruit weight. This is in contrast to the publication by Shetty et al. (Crop Science 42:2174-2183 (2002)), wherein a relationship between high number of fruits was studied. Shetty et al. do not disclose actual yield data for PI 169383, but merely conclude on it's performance. Furthermore, Shetty et al. compared the genebank accessions, including PI 169383 with late-maturing, low-yielding, gynoecious inbreds. One of the inbreds for instance was WI 2757, which produced 27.000 marketable fruits per ha. (see Shetty et al. table 5), which is equivalent to 2.7 marketable fruits per square meter. In comparison, PI 169383 in the present study was found to produce 3.4 marketable fruits per square meter, whereas the inbred lines used in the present study exhibit much higher yields, in the order of 7 marketable fruits per square meter and more. As a result of their experimental set-up, Shetty et al. considered PI 169383 to be a higher yielding accession. However, when compared to normal high yielding inbreds, PI 169383 is a low yielding accession in terms of fruit weight per plant or per $m^2$, as well as in fruit number per plant. This is underscored by the data provided in the Example of the present invention which put the observation of Shetty et al. into proper perspective indicating that PI 169383 also produces fewer fruits compared to cultivated cucumber.

Figure 2:
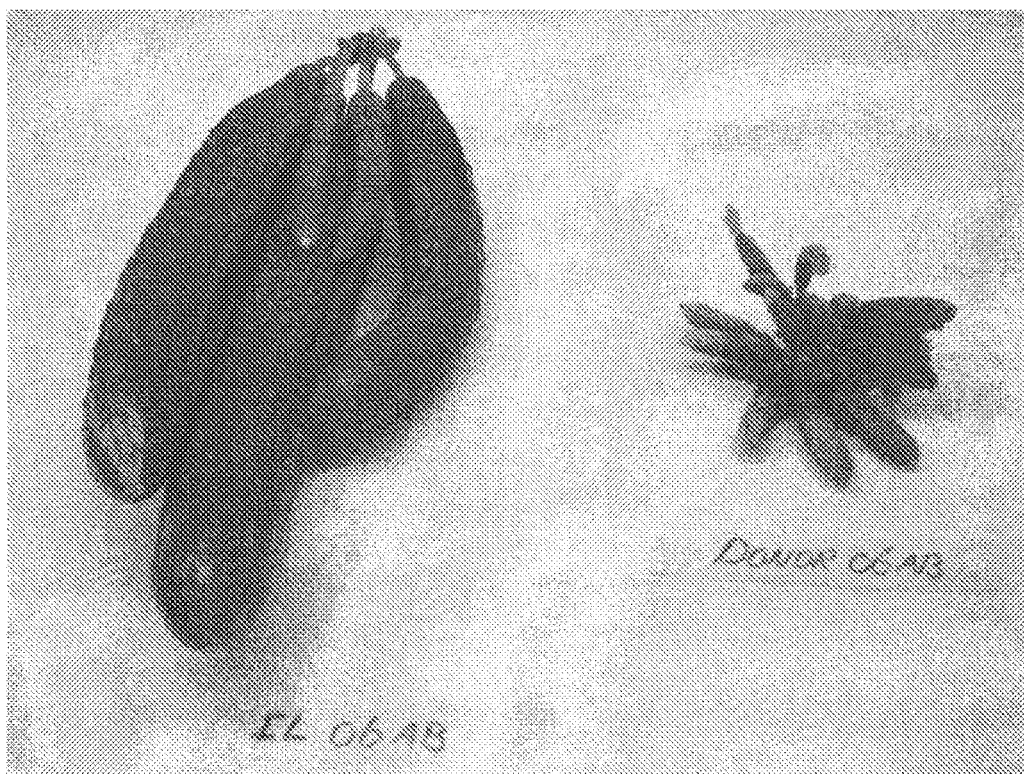
FIG. 2 shows a photograph of fruits obtained from an IL that is close to the commercial variety (left hand side, indicated by "IL 06AB") and the donor PI169383 (right hand side, indicated by "Donor 06AB"). The fruits are collected from one armpit of the plant.
Figure 3:
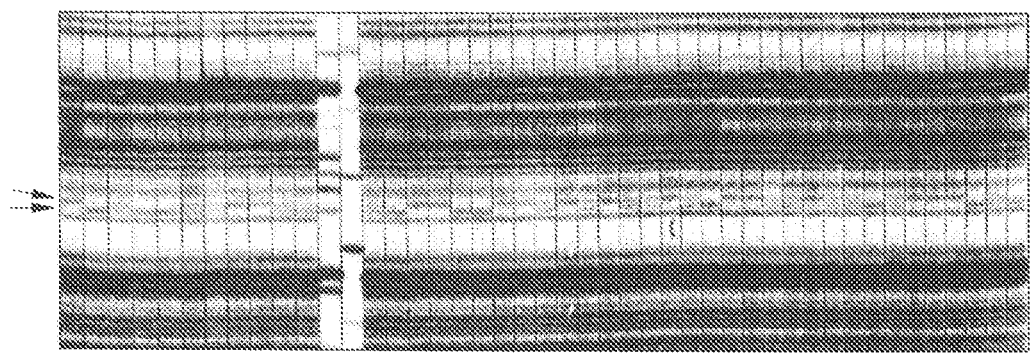
FIG. 3 shows a partial (clipped) image of an AFLP gel demonstrating the AFLP pattern of the genome of selected cucumber plants amplified with primer combination E12/M24 as defined herein. Fragments with a length of 176 and 177 base pairs are indicated by adjacent arrows (left), and indicate the bi-allelic marker E12/M24-F-177-P2/E12/M24-F-176-P1. Gels were run from top to bottom.
Figure 4:
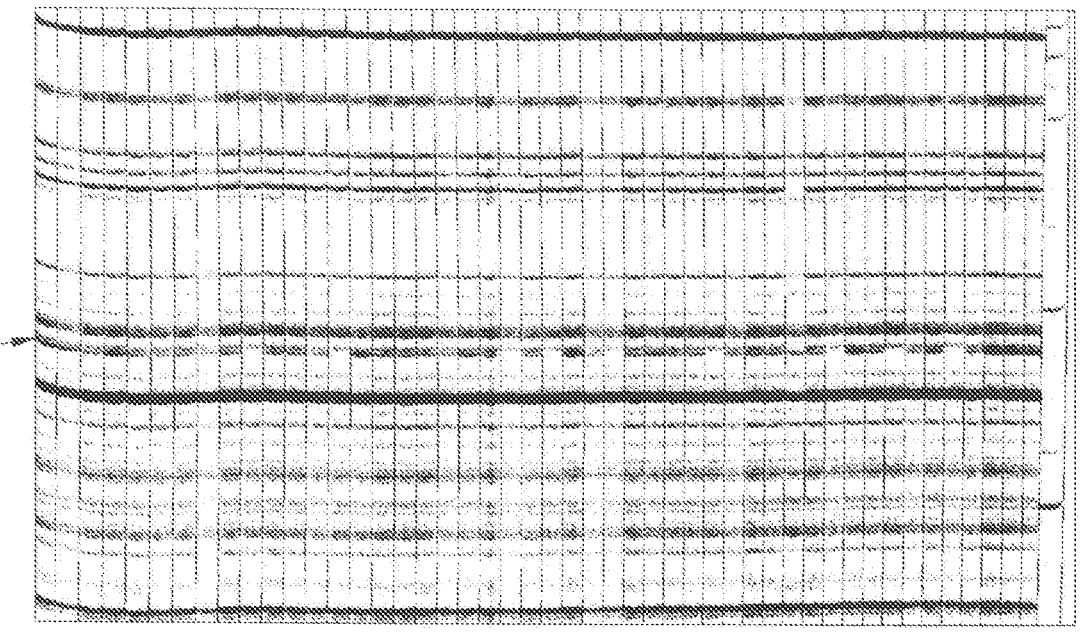
FIG. 4 shows a partial (clipped) image of an AFLP gel demonstrating the AFLP pattern of the genome of selected cucumber plants amplified with primer combination E11/M62 as defined herein. The fragment of 200 base pairs indicative of marker E11/M62-F-200-P1 is indicated by an arrow (left).

But even when it would be considered that PI 169383 exhibits high yield percentage by number of cucumbers, it is still unexpected that PI 169383 contains a genetic region that is responsible for a high yield in weight. After all, a negative correlation between quantity and weight is inherent to plant breeding. One example is given in FIG. 2 herein below, wherein it is depicting that the donor line PI 169383 produces many small cucumbers in a truss, whereas the introgression line (IL) produces fewer large fruit in a truss. Another well-known example includes equal yield weight from cherry vs beef tomatoes, despite the substantial difference in fruit size. Hence it was unexpected that any high yield weight introgression could be derived from PI 169383, which was reported to exhibit high yield number.

In cucumber breeding, yield number and yield weight are traits that are considered separately. The weight per fruit is a fixed value determined by market requirements, and high yield in weight is more important that high yield in numbers (of small cucumbers).

The present inventors discovered that in Cucumber accession PI 169383, a gene or regulatory sequence associated with increased yield is present on linkage group 4. According to Horejsi et al. (2000), linkage group 4 of *Cucumis sativus* L also comprises genes for resistance to downy mildew (dm) resistance. LG 4 may be further characterized by (either) one or a combination of the following well known markers: 1) CSC443/H3 (RFLP marker; Bradeen, et al., 2001, *Genome* 44:111-119); 2) BC551.550 (RAPD marker; Park et al., 2000, *Genome* 43:1003-1010); 3) PER (isozyme; Bradeen et al. supra).

A definitive chromosome number has not yet been assigned to the cucumber chromosome on which the QTL for increased yield is located. However, the chromosome may be designated by reference to the linkage group (LG 4) on which these and other genomic regions are located. The term linkage group is used herein to refer to a physical genomic unit on which the yield improving-conferring alleles are located, and which has the same hierarchical level as a chromosome.

A first method would comprise introgressing the QTL for increased yield from a plant of Cucumber accession PI 169383 into a plant of a cucumber line of interest. This will result in a situation wherein the QTL is in the genetic background of the cucumber line of interest. The establishment of the proper introgression in offspring plants may be monitored by using the QTL specific markers.

Recombination is the exchange of information between two homologous chromosomes during meiosis. In a recombinant plant, DNA that is originally present on a specific location within the chromosome is exchanged for DNA from another plant (i.e. maternal for paternal or vice versa). In order to exchange only the required material, and maintain the valuable original information on the chromosome as much as possible, will usually require two crossover events. The normal way to find such a recombinant, is to screen a population of F2-plants. This population must be of sufficient size in order to detect the rare (low frequency) double recombinants. The frequency of recombination may be calculated as follows. For instance, a recombinant in a 10 cM area can be found with a frequency of 10% (1 centimorgan is defined as 1% recombinant progeny in a testcross).

The present invention now provides for better models for marker assisted selection (MAS). The invention therefore relates to methods of plant breeding and to methods to select plants, in particular cucumber plants, particularly cultivated cucumber plants as breeder plants for use in breeding programs or cultivated cucumber plants for having desired genotypic or potential phenotypic properties, in particular related to producing valuable cucumber fruits, also referred to herein as agronomically desirable plants. Herein, a cultivated plant is defined as a plant being purposely selected or having been derived from a plant having been purposely selected in agricultural or horticultural practice for having desired genotypic or potential phenotypic properties, in particular a plant obtained by inbreeding.

Since the yield-improving QTL is an additive trait (the hybrid expresses a phenotype in between the two parents), it can be monitored in the F1 or BC1 by measuring the yield of the plants. However, since this will require many weeks of cultivation under controlled conditions, it is of particular advantage that the establishment of the proper introgression in offspring plants may be monitored by using the QTL-specific markers as provided herein, either in cis or in trans coupling as explained below. By using MAS or MAB methods, the skilled person is therefore provided with methods for selecting plants.

The present invention thus also provides methods for selecting a plant of the species *Cucumis sativus* exhibiting increased yield comprising detecting in said plant the presence on linkage group (chromosome) 4 of the yield-improving QTL as defined herein. In a preferred method of the invention for selecting such a plant the method comprises:
a) providing a sample of genomic DNA from a cucumber plant;
b) detecting in said sample of genomic DNA at least one molecular marker linked to the yield-improving QTL.

The step of providing a sample of genomic DNA from a cucumber plant may be performed by standard DNA isolation methods well known in the art.

The step of detecting a molecular marker (step b) may, in a preferred embodiment, comprise the use of a set of bi-directional primers that were used in the AFLP method to produce the amplification product that represents the marker for the QTL. Such a set of primers is herein referred to as the primers that define the AFLP marker or marker-specific primers. Bi-directional means that the orientation of the primers is such that one functions as the forward and one as the reverse primer in an amplification reaction of nucleic acid.

Alternatively, the step of detecting a molecular marker (step b) may in another preferred embodiment, comprise the use of a nucleic acid probe having a base sequence which is substantially complementary to the nucleic acid sequence defining said molecular marker and which nucleic acid probe specifically hybridizes under stringent conditions with a nucleic acid sequence defining said molecular marker. A suitable nucleic acid probe may for instance be a single strand of the amplification product corresponding to the marker.

The step of detecting a molecular marker (step b) may also comprise the performance of a nucleic acid amplification reaction on said genomic DNA to detect said QTL. This can suitable be done by performing a PCR reaction using a set of marker-specific primers. In a preferred embodiment, said step b) comprises the use of at least one set of primers defining an AFLP marker for said QTL, or a set of primers which specifically hybridize under stringent conditions with a nucleic acid sequence of an AFLP marker for said QTL.

The step of detecting an amplified DNA fragment having the predicted length or the predicted nucleic acid sequence of step d) is preferably performed such that the amplified DNA fragment has a length that corresponds (plus or minus a few bases, e.g. a length of one, two or three bases more or less) to the expected length as based on a similar reaction with the same primers with the DNA from the plant in which the marker was first detected or the nucleic acid sequence that corresponds (has a homology of more than 80%, preferably more than 90%, more preferably more than 95%, even more preferably more than 97%, still more preferably more than 99%) to the expected sequence as based on the sequence of the marker associated with that QTL in the plant in which said marker was first detected. The skilled person is aware that markers that are absent in plants having the introgression as defined herein (donor plans), while they are present in the plants receiving the introgression (recipient plants) (so-called trans-markers), may also be useful in assays for detecting the introgression among offspring plants, although testing the absence of a marker to detect the presence of a specific introgression is not optimal.

The step of detecting an amplified DNA fragment having the predicted length or the predicted nucleic acid sequence may be performed by standard gel-electrophoresis techniques or by using automated DNA sequencers. The methods need not be described here as they are well known to the skilled person. It should be noted that the marker is defined based on its primer sequences in combination with the length of the amplification product and the position of the marker relative to other markers on a linkage map.

Molecular Markers and QTLs

Molecular markers are used for the visualisation of differences in nucleic acid sequences. This visualisation is possible due to DNA-DNA hybridisation techniques after digestion with a restriction enzyme (RFLP) and/or due to techniques using the polymerase chain reaction (e.g. STS, microsatellites, AFLP). All differences between two parental genotypes will segregate in a mapping population (e.g., $BC_1$, $F_2$) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a short genetic distance between markers on a chromosome. Comparing all recombination frequencies will result in the most logical order of the molecular markers on the chromosomes. This most logical order can be depicted in a linkage map. A group of adjacent or contiguous markers on the linkage map that is associated with an increased yield, pinpoints the position of a QTL associated with increased yield.

The markers identified herein may be used is various aspects of the invention as will now be illustrated. Aspects of the invention are not limited to the use of the markers identified herein. It is stressed that the aspects may also make use of markers not explicitly disclosed herein or even yet to be identified. Other than the genetic unit "gene", on which the phenotypic expression depends on a large number of factors that cannot be predicted, the genetic unit "QTL" denotes a region on the genome that is directly related to a phenotypic quantifiable trait. Thus, while genes per se bear little or no relation to plant breeding, a QTL is directly applicable to plant breeding.

The QTL as identified herein is located on linkage group 4 and its location is best characterized by a number of otherwise arbitrary markers. In the present investigations amplified fragment length polymorphism (AFLP) markers, single nucleotide polymorphisms (SNPs), and insertion mutation markers were used, although restriction fragment length polymorphism (RFLP) markers, microsatellite markers (e.g. SSRs), sequence-characterized amplified region (SCAR) markers, cleaved amplified polymorphic sequence (CAPS) markers or isozyme markers or combinations of these markers might also have been used. In general, a QTL may span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace amongst a population of offspring plants those plants that have the genetic potential for exhibiting a particular phenotypic trait. By providing a non-limiting list of markers, the present invention thus provides for the effective utility of the QTLs in a breeding program.

A marker is specific for a particular line of breed. Thus, a specific trait is associated with a particular marker. The markers as indicated in the present application do not only indicate the location of the QTL, they also correlate to the presence of the specific phenotypic trait in a plant. It is important to note that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e. one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL are set. Thus, it is also possible to indicate the location of the QTL by other markers located within that specified region.

It is further important to note that the contiguous genomic markers can also be used to indicate the presence of the QTL (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the QTL, e.g. falling within the physically boundaries of the genomic region spanned by the markers having established LOD scores above a certain threshold thereby indicating that no or very little recombination between the marker and the QTL occurs in crosses; as well as any marker in linkage disequilibrium to the QTL; as well as markers that represent the actual causal mutations within the QTL, may be used in MAS procedures. This means that the markers identified in the application as associated to the QTLs, such as the AFLP markers E12/M24-F-063-P2; E11/M62-F-200-P1; E12/M24-F-177-P2; E12/M24-F-176-P1; E25/M13-F-128-P2; E21/M16-F-080-P2, for the yield-improving QTL, are mere examples of markers suitable for use in MAS procedures. Also markers E22M12-F-278-P1 and E22/M12-F-092-P2 may be used as they show linkage to the trait as can be seen in FIG. 1. These markers may suitably be "cis markers" indicating that their presence coincides with the presence of the QTL. Moreover, when the QTL, or the specific trait-conferring part thereof, is introgressed into another genetic background (i.e. into the genome of another plant line), then some markers may no longer be found in the offspring although the trait is present therein, indicating that such markers are outside the genomic region that represents the specific trait-conferring part of the QTL in the original parent line only and that the new genetic background has a different genomic organisation. Such markers of which the absence indicates the successful introduction of the genetic element in the offspring are called "trans markers" and may be equally suitable in MAS procedures under the present invention.

The haplotype of the yield QTL of the present invention with respect to the markers is: E12/M24-F063-P2 cis (presence of marker); E11/M62-F-200-P1 trans (absence of marker); E12/M24-F-177-P2 cis (presence of marker); E12/M24-F-176-P1 trans (absence of marker); E25/M13-F-128-P2 cis (presence of marker); E22M12-F-278-P1 trans (absence of marker); E22/M12-F-092-P2 cis (presence of marker); E21/M16-F-080-P2 cis (presence of marker). P1 or P2 indicates the parent label (genomic background) of the marker, wherein P1 is the recurrent parent and P2 is the donor parent.

Upon the identification of the QTL, the QTL effect (the improved yield) may for instance be confirmed by assessing the yield of $BC_2S_1$ progenies segregating for the QTLs under investigation. Preferably, detecting the presence of a QTL of the invention is performed with at least one of the markers for a QTL as defined herein. The present invention therefore also relates to a method for detecting the presence of a QTL for improved yield in cucumber by the use of the said markers.

The nucleotide sequence of the QTL of the present invention may be resolved by determining the nucleotide sequence of one or more markers associated with said QTL and designing internal primers for said marker sequences that may then be used to further determine the sequence the QTL outside of said marker sequences. For instance the nucleotide sequence of AFLP markers may be obtained by isolating said markers from the electrophoresis gel used in the determination of the presence of said markers in the genome of a subject plant, and determining the nucleotide sequence of said markers by for instance dideoxy chain terminating methods, well known in the art.

In embodiments of methods for detecting the presence of a QTL in a cucumber plant, the method may also comprise the steps of providing a oligonucleotide or polynucleotide capable of hybridizing under stringent hybridization conditions to a nucleic acid sequence of a marker linked to said QTL, contacting said oligonucleotide or polynucleotide with digested genomic nucleic acid of a cucumber plant, and determining the presence of specific hybridization of said oligonucleotide or polynucleotide to said digested genomic nucleic acid.

Preferably said method is performed on a nucleic acid sample obtained from said cucumber plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a cucumber plant.

In principle, individual AFLP markers as used herein have a designated marker code. This code defines two primers, optionally in combination with a figure indicating the length of the amplification product of the primers in a defined accession (see also description for Table 1 hereinabove). An AFLP marker thus defines a single or double-stranded DNA fragment as obtained by performing an amplification reaction on cucumber genomic DNA, which in the case of the indicated accession results in a fragment of the indicated length. Furthermore, the marker comprises in a 5'-3' direction a sequence consisting of a first primer sequence, a cucumber-specific DNA sequence and a second primer sequence, and its complement. The cucumber-specific DNA sequence thus being flanked by the two primers. The term "cucumber-specific DNA sequence" denotes the nucleotide sequence of the region flanked by the respective primers and represents the sequence amplified from cucumber accession PI 169383, or a sequence having a sequence homology thereto of at least 90%, preferably at least 95%, most preferably at least 98%.

Production of Cucumber Plants Having Increased Yield by Transgenic Methods

According to another aspect of the present invention, a nucleic acid (preferably DNA) sequence comprising QTL may be used for the production of a cucumber plant having increased yield. In this aspect, the invention provides for the use of QTLs as defined herein or yield improving parts thereof, for producing a cucumber plant having improved yield, which use involves the introduction of a nucleic acid sequence comprising said QTL in a suitable recipient plant. As stated, said nucleic acid sequence may be derived from a suitable donor plant. A suitable source according to the present invention for the yield-improving QTL is cucumber landrace PI 169383, originating from Turkey. Such plants may for instance be obtained through T. C. Wehner, cucumber gene curator for the Cucurbit Genetics Cooperative (CGC), Department of Horticultural Science, North Carolina State University, Raleigh, N.C. 27695-7609 U.S.A. or the Germplasm Resources Information Network (GRIN) hosted by the USDA's National Germplasm Resources Laboratory, Beltsville, Md.

The nucleic acid sequence that comprises a QTL for improving yield, or a yield-improving part thereof, may be transferred to a suitable recipient plant by any method available. For instance, the said nucleic acid sequence may be transferred by crossing a plant of line PI 169383 with a selected breeding line of which the yield is to be improved, (i.e. by introgression), by transformation, by protoplast fusion, by a doubled haploid technique or by embryo rescue or by any other nucleic acid transfer system, optionally followed by selection of offspring plants comprising the QTL and exhibiting increased yield. For transgenic methods of transfer a nucleic acid sequence comprising a QTL for increased yield may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a QTL for increased yield, which vector may comprise a for yield improving gene that is under control of or operatively linked to a regulatory element, such as a promoter. The expression vector may contain one or more such operably linked gene/regulatory element combinations, provided that at least one of the genes contained in the combinations encodes for improved yield. The vector(s) may be in the form of a plasmid, and can be used, alone or in combination with other plasmids, to provide transgenic plants that exhibit improved yield, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. Methods of introducing expression vectors into plant tissue include the direct infection or co-cultivation of plant cells with *Agrobacterium tumefaciens*. Descriptions of *Agrobacterium* vectors systems and methods for *Agrobacterium*-mediated gene transfer are provided in U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993.

General methods of culturing plant tissues are provided for example by Miki et al., 1993 and by Phillips, et al., 1988. A proper reference handbook for molecular cloning techniques and suitable expression vectors is Sambrook and Russell, 2001.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Another method for introducing DNA to plants is via the sonication of target cells. Alternatively, liposome or spheroplast fusion has been used to introduce expression vectors into plants. Direct uptake of DNA into protoplasts using $CaCl_2$ precipitation, polyvinyl alcohol or poly-L-ornithine has also been reported. Electroporation of protoplasts and whole cells and tissues has also been described.

Other well known techniques such as the use of BACs, wherein parts of the cucumber genome are introduced into bacterial artificial chromosomes (BACs), i.e. vectors used to clone DNA fragments (100- to 300-kb insert size; average, 150 kb) in *Escherichia coli* cells, based on naturally occurring F-factor plasmid found in the bacterium *E. coli*. may for instance be employed in combination with the BIBAC system to produce transgenic plants.

Following transformation of cucumber target tissues, expression of the above described selectable marker genes allows for preferential selection of transformed cells, tissues and/or plants, using regeneration and selection methods now well known in the art.

Production of Cucumber Plants Having Improved Yield by Non-Transgenic Methods

In an alternative embodiment for producing a cucumber plant having improved yield, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbreeded in nature, is tissue cultured into a hybrid plant exhibiting the desirable combination of traits. More specifically, a first protoplast can be obtained from a cucumber plant of PI 169383. A second protoplast can be obtained from a second cucumber or other plant variety, preferably a cucumber line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising the QTL as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants.

The present invention also relates to a method for improving the yield of a plant of a cucumber breeding line, comprising the steps of:

a) crossing a plant of a cucumber breeding line with a plant of cucumber line PI 169383;

b) selecting a progeny cucumber plant resulting from said crossing having an introgression from cucumber accession PI 169383 on linkage group 4 associated with increased yield;

c) selfing and/or backcrossing said progeny cucumber plant selected in step (b) using said cucumber breeding line as a recurrent parent;

d) selecting a progeny cucumber plant resulting from the selfing or backcrossing in step (c) having an introgression from cucumber accession PI 169383 on linkage group 4 associated with increased yield e) repeating said steps of selfing and/or backcrossing and selection of steps (c) and (d) to provide a plant of a cucumber breeding line essentially homozygous for said introgression, wherein at least one selection as performed in steps (b) or (d) is performed by marker-assisted selection.

In a preferred embodiment of such a method, said cucumber breeding line is an elite line.

In an alternative preferred embodiment of the above method, the marker-assisted selection procedure comprises the selection for AFLP markers E12/M24-F-063-P2; E11/M62-F-200-P1; E12/M24-F-177-P2; E12/M24-F-176-P1; E25/M13-F-128-P2; and/or E21/M16-F-080-P2.

A preferred embodiment of such a method comprises the transfer by introgression of said nucleic acid sequence from PI 169383 as a donor cucumber plant into a recipient cucumber plant by crossing said plants. The introgression of the nucleic acid sequence comprising the QTL according to the invention may thus suitably be accomplished by using traditional breeding techniques. The QTL is preferably introgressed into commercial cucumber varieties by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of the QTL of the present invention or markers associated therewith. MAS can also be used to develop near-isogenic lines (NIL) harboring the QTL of interest, allowing a more detailed study of each QTL effect and is also an effective method for development of backcross inbred line (BIL) populations. Cucumber plants developed according to this embodiment can advantageously derive a majority of their traits from the recipient plant, and derive improved yield from the donor plant.

As discussed briefly above, traditional breeding techniques can be used to introgress a nucleic acid sequence encoding for improved yield into a recipient cucumber plant requiring yield improvement. In one method, which is referred to as pedigree breeding, a donor cucumber plant that exhibits improved yield and comprising a nucleic acid sequence encoding for the QTL associated with improved yield as defined herein is crossed with a recipient cucumber plant (preferably a plant of an elite line) that exhibits agronomically desirable characteristics, such as, but not limited to, disease resistance, insect resistance, valuable fruit characteristics, etc. The resulting plant population (representing the $F_1$ hybrids) is then self-pollinated and set seeds ($F_2$ seeds). The $F_2$ plants grown from the $F_2$ seeds are then screened for improved yield. The population can be screened in a number of different ways.

First, the population can be screened using a traditional yield assays. Such assays are known in the art. Second, marker-assisted selection can be performed using one or more of the hereinbefore-described molecular markers to identify those progeny that comprise a nucleic acid sequence encoding for improved yield as defined herein. Other methods, referred to hereinabove by methods for detecting the presence of a QTL may be used. Also, marker-assisted selection can be used to confirm the results obtained from the yield assays, and therefore, several methods may also be used in combination.

Inbred cucumber plant lines having improved yield can be developed using the techniques of recurrent selection and backcrossing, selfing and/or dihaploids or any other technique used to make parental lines. In a method of recurrent selection and backcrossing, the improved yield-conferring genetic element as disclosed herein can be introgressed into a target recipient plant (the recurrent parent) by crossing the recurrent parent with a first donor plant, which differs from the recurrent parent and is referred to herein as the "non-recurrent parent". The recurrent parent is a plant of which the yield is to be improved and possesses agronomically desirable characteristics, such as, but not limited to disease resistance, insect resistance, valuable fruit characteristics, etc. The non-recurrent parent is a plant of line PI 169383 and comprises a nucleic acid sequence that encodes for improved yield. Alternatively, the non-recurrent parent can be any plant variety or inbred line that is cross-fertile with the recurrent parent and has acquired the QTL for improved yield in an earlier cross with a plant of line PI 169383. The progeny resulting from a cross between the recurrent parent and non-recurrent parent are backcrossed to the recurrent parent. The resulting plant population is then screened for the desired characteristics, which screening may occur in a number of different ways. For instance, the population can be screened using phenotypic screens as known in the art. Alternatively, instead of using phenotypic assays, marker-assisted selection (MAS) can be performed using one or more of the hereinbefore described molecular markers, hybridization probes or polynucleotides to identify those progeny that comprise a nucleic acid sequence encoding improved yield.

Following screening, the $F_1$ hybrid plants that exhibit an improved yield phenotype or, more preferably, genotype and thus comprise the requisite nucleic acid sequence encoding for increased yield are then selected and backcrossed to the recurrent parent for a number of generations in order to allow for the cucumber plant to become increasingly inbred. This process can be performed for two to five or more generations. In principle the progeny resulting from the process of crossing the recurrent parent with the non-recurrent parent are heterozygous for one or more genes that encode for improved yield.

In general, a method of introducing a desired trait into a hybrid cucumber variety comprises the steps of:
  (a) crossing an inbred cucumber parent with another cucumber plant that comprises one or more desired traits, to produce F1 progeny plants, wherein the desired trait is improved yield as conferred by the yield improving QTL from PI 169383;
  (b) selecting said F1 progeny plants that have the desired trait to produce selected F1 progeny plants, preferably using molecular markers as defined herein;
  (c) backcrossing the selected progeny plants with said inbred cucumber parent plant to produce backcross progeny plants;
  (d) selecting for backcross progeny plants that have the desired trait and morphological and physiological characteristics of said inbred cucumber parent plant, wherein said selection comprises the isolation of genomic DNA and testing said DNA for the presence of at least one molecular marker for the QTL as defined above;
  (e) repeating steps (c) and (d) two or more times in succession to produce selected third or higher backcross progeny plants;
  (f) optionally selfing selected backcross progeny in order to identify homozygous plants;
  (g) crossing at least one of said backcross progeny or selfed plants with another inbred cucumber parent plant to generate a hybrid cucumber variety with the desired trait and all of the morphological and physiological characteristics of hybrid cucumber variety when grown in the same environmental conditions.

As indicated, the last backcross generation may be selfed in order to provide for homozygous pure breeding (inbred) progeny having improved yield. Thus, the result of recurrent selection, backcrossing and selfing is the production of lines that are genetically homogenous for the genes associated with improved yield as well as other genes associated with traits of commercial interest.

It should be noted that heterozygous plants also exhibit improved yield, and such plants are therefore also an aspect of the present invention.

Cucumber Plants and Seeds

The goal of plant breeding is to combine various desirable traits in a single variety or hybrid. For commercial crops, these traits may include resistance to diseases and insects, tolerance to heat and drought, reducing the time to crop maturity, greater yield, and better agronomic quality. Uniformity of plant characteristics such as germination and stand establishment, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid cucumber variety in a cucumber plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid cucumber plants can then be generated from this hybrid seed supply.

Using the methods as described above, the skilled person will be able to produce the required inbred lines and from those produce the commercial (F1) hybrid seeds by crossing said inbred lines.

EXAMPLES

Yield-Improving Introgressions

Development of the IL Population

An exotic donor PI69383 was crossed with a commercial parental line, which is the mother line of a commercial cucumber hybrid variety. Introgression lines were developed using AFLP markers to select for genome coverage and overlapping segments during BC1, BC2 and subsequent selfings generations (depending on the IL, 1 or 2 selfings were performed). The BC1 generation was used to obtain a genetic map for cucumber. No common markers with other maps were found and therefore no chromosome numbers could be assigned. The linkage groups as referred to herein refer to random linkage group numbers. The selection for genome coverage resulted in the selection of 30 introgression lines (IL).

The IL were crossed with the recurrent parent (F1 IL) resulting in a line that is heterozygous for the donor segment, but is homozygous for the rest of the genome. The IL were also crossed with the other commercial parent of the variety (father line), resulting in a hybrid (HY IL) that is heterozygous for the donor segment, and for the rest of the genome.

In the present experimental setup, so-called hybrid ILs (i.e. parental line 1 harbouring the introgression crossed with parental line 2 of the original variety Accolade) performed very well (See Table 1).

Phenotyping of the Population

The 30 IL were grown in the greenhouse in 2 replicate blocks, each block of 5.75 m² contained 8 plants, resulting in a planting density of 1.39 plants per square meter. The QTL was only detected in the ILs during early spring experiments, and not in summer season experiments.

In order to determine the production in kg/m², the fruit weight and the harvest earliness for long cucumber, the fruits of the ILs were harvested 2 or 3 times a week during a period of at least 2 months wherein the plant produces fruits at harvest stage (fruits with a diameter of at least 4 cm in the middle of the fruit; fruits which stop growing for 3 days are also harvested, even if the diameter of 4 cm is not reached), and every harvest the yield as total weight of the harvest and as number of fruits was determined. Results are provided in Table 1, wherein values indicated are mean values per block.

The yield in terms of production (P) was expressed as yield/m² and was calculated as follows:

$$P = \frac{\text{(total wt. (in kg) per block per cultivation)}}{\text{(no. of plants per block)}} \times \text{(plant density per m}^2\text{)}$$

Fruit weight = total weight in kg/total no. of fruits

Fruits were harvested by cutting the fruit peduncle at 1 cm distance from the fruit. The yield was measured within 2 hours from harvesting using a balance. The harvest earliness is the first harvest date of a field in days after sowing.

TABLE 1

Yields of introgression lines.

| IL number | Yield in kg fruits/block | Yield in no. fruits/block | IL number | Yield in kg fruits/block | Yield in no. fruits/block |
|---|---|---|---|---|---|
| Control BC | 41.3 | 155.8 | Parent line | 50.8 | 177.5 |
| Control* | 42.3 | 151.5 | HYIL 1-1 | 45.9 | 155.0 |
| Control** | 19.5 (−) | 107.8 (−) | HYIL 2-1 | 45.3 | 171.5 |
| LIL 1-1 | 41.7 | 141.0 | HYIL 2-2 | 55.5 | 187.5 |
| SIL 1-1 | 39.1 | 141.5 | HYIL 3-1 | 55.4 | 206.0 (+) |
| F1 IL 1-1 | 43.7 | 146.5 | HYIL 4-1 | 60.5 (+) | 207.5 (+) |
| LIL 2-1 | 38.9 | 150.0 | HYIL 4-2 | 52.3 | 184.5 |
| LIL 2-2 | 27.0 (−) | 104.5 (−) | HYIL 5-1 | 45.9 | 163.0 |
| SIL 2-1 | 39.0 | 154.0 | HYIL 6-1 | 47.7 | 170.0 |
| SIL 2-2 | 34.4 (−) | 130.5 (−) | HYIL 6-3 | 47.9 | 166.5 |
| F1 IL 2-1 | 38.9 | 155.5 | HYIL 7-1 | 51.1 | 174.5 |
| F1 IL 2-2 | 38.2 | 141.5 | HYIL 8-1 | 45.9 | 156.0 |
| LIL 3-1 | 43.9 | 182.0 (+) | | | |
| SIL 3-1 | 37.2 | 135.5 | | | |
| SIL 3-2 | 48.2 (+) | 187.0 (+) | | | |
| SIL 3-3 | 39.7 | 160.5 | | | |
| SIL 3-4 | 46.6 | 190.0 (+) | | | |
| SIL 3-5 | 48.6 (+) | 217.5 (+) | | | |
| SIL 3-6 | 43.4 | 172.0 | | | |
| F1 IL 3-1 | 41.2 | 162.0 | | | |
| LIL 4-1 | 54.4 (+) | 229.0 (+) | | | |
| LIL 4-2 | 51.6 (+) | 214.5 (+/−) | | | |
| SIL 4-1 | 38.7 | 154.5 | | | |
| SIL 4-2 | 56.2 (+) | 229.5 (+) | | | |
| SIL 4-3 | 53.9 (+) | 232.0 (+) | | | |
| SIL 4-4 | 46.9 | 197.5 (+) | | | |
| SIL 4-5 | 46.2 | 169.5 | | | |
| F1 IL 4-1 | 49.4 (+) | 187.0 (+) | | | |
| F1 IL 4-2 | 44.5 | 178.5 | | | |
| LIL 5-1 | 36.3 | 153.5 | | | |
| SIL 5-1 | 38.7 | 160.0 | | | |
| SIL 5-2 | 36.8 | 152.0 | | | |
| SIL 5-3 | 45.4 | 183.0 (+) | | | |
| SIL 5-4 | 37.0 | 148.0 | | | |

TABLE 1-continued

Yields of introgression lines.

| IL number | Yield in kg fruits/block | Yield in no. fruits/block | IL number | Yield in kg fruits/block | Yield in no. fruits/block |
|---|---|---|---|---|---|
| F1 IL 5-1 | 40.5 | 156.0 | | | |
| LIL 6-1 | 34.4 (−) | 148.0 | | | |
| LIL 6-3 | 38.6 | 137.5 | | | |
| SIL 6-1 | 45.9 | 171.5 | | | |
| F1 IL 6-1 | 32.4 (−) | 126.5 (−) | | | |
| F1 IL 6-3 | 39.9 | 145.5 | | | |
| LIL 7-1 | 48.9 (+) | 188.5 (+) | | | |
| F1 IL 7-1 | 51.8 (+) | 183.5 (+) | | | |
| LIL 8-1 | 39.5 | 152.5 | | | |
| F1 IL 8-1 | 38.9 | 154.0 | | | |

The top row indicates the control values, values higher than the control are indicated by (+), values lower than the control are indicated by (−).
Control BC = line Pyr42;
Control* = proprietary parent of commercial hybrid Accolade;
Control ** = PI69383;
Parent line = Commercial hybrid Accolade.

Figure 5:
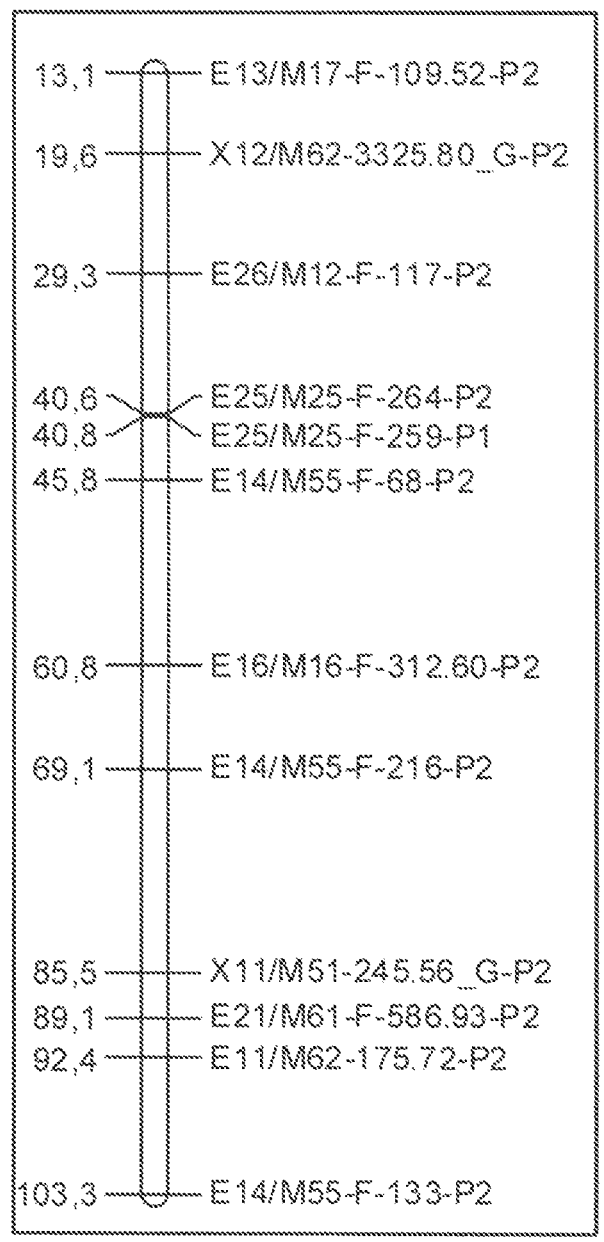
FIG. 5 shows the linkage map for chromosome 3 (linkage group 3) of *Cucumis sativus*. This application also contemplates the use of chromosome substitutions of chromosome 3. In such a substitution line, all nuclear DNA originates from the recurrent parent, except for the chromosome characterised by markers in linkage group 3. All DNA associated with markers listed in the linkage map, which are preferably unique and genetically linked, originates from the donor parent PI169383.

This application also contemplates the use of chromosome substitutions of chromosome 3. In such a substitution line, all nuclear DNA originates from the recurrent parent, except for the chromosome characterised by markers in linkage group 3 (see FIG. 5). Subsequent experiments showed that LIL3-1 (a chromosome substitution line wherein the chromosome corresponding to linkage group 3 was substituted by donor material) and offspring thereof, resulted in plants exhibiting higher yield in kg and vigour relative to the controls. In particular, this particular introgression exhibited outstanding performance in hybrid phase (when crossed with the 2nd parent of the original variety) compared to any other (hybrid) IL in the current trial. Any and all markers as indicated in FIG. 5 may in principle be used to indicate the presence or absence of the chromosome corresponding to linkage group 3 in a plant of the invention.

Construction of High Resolution IL Panel for Fine Mapping of LIL 4-2

LIL 4-2 was Considered the Major IL of Interest.

Fine-mapping of the yield QTL, was performed by providing a "High Resolution IL panel". The panel consisted of lines with smaller introgressions derived from line LIL 4-2.

Leaf material of 184 F2 individuals of a LIL 4-2× recurrent parent was tested. DNA was isolated and EcoRI/MseI templates were generated.

The selection of recombinants was executed in two steps. In the first step all individuals were screened with various primer combinations (PCs) (E12/M24; E18/M15; E14/M60; E11/M62; E13/M17; E25/M13; E22/M12; E21/M16) amplifying at least one marker located in each of the three LG4 introgression segments of LIL 4-2 (see FIG. 1) and the introgression segment on LG 5 (LIL 4-2 contains an undesired donor segment on LG 5 which is presented in FIG. 2). Ninety six plants were selected for further analysis based on the following criteria:

1) Donor segment LG 5 is not homozygous present
2) Plant contains a maximum of 3 donor segments (one of the 3 donor segments on LG 4)

This selection of 96 F2 plants was subsequently screened with two more PCs containing markers positioned on the LG4 donor segments. Based on the total data set of these 96 F2 plants two sets of plants were selected for propagation to F3. A set consisting of 47 individuals was selected for further study.

Marker Detection

AFLP analysis was performed according to Vos et al., (1995). Nucleic Acids Res. 23: 4407-4414.

Marker Sequences

Overview of the sequences of the AFLP markers linked to LIL 4-2. The sequences include the forward and reverse "core primers" E (having the EcoR1 restriction site) and M (having the Nisei restriction site). The sequence of the primers is underlined. The reverse primer is included in the sequence as the reverse complement. The selective nucleotides with which the "core primers" were extended are double underlined.

```
E18/M15-F-089-P2
GACTGCGTACCAATTCCTCTAGTACTTTCTTCTGTTTCTCTTATTTCCTT

TCCTGAATATAATTATGTTACTCAGGACTCATC  (SEQ ID NO:1)

E14/M60-F-226A-P1 (for AFLP E14/M60-226 two
different sequences were obtained, possibly due
to a background band)
GACTGCGTACCAATTCATTCTAAATTCAAATTCCGTCCTAAATTGTTGAT

TTGGTAAGGAAGTTGTGAGAATTGTTTTGGGATGGGATGAGATAATTGT

GGTAGGCTGTATTGCTTTCCATTGTTGTGTATGTGTATGTGATATTGTAT

TGTTGTTCTTTTTTGGTTGAGTTTGGGTGCTCTTTTTGCCTCCTGGGTTT

ATGGTTGGAGTTACTCAGGACTCATC  (SEQ ID NO:2)

E14/M60-F-226B-P1 (for AFLP E14/M60-226 two
different sequences were obtained, possibly due
to a background band)
GACTGCGTACCAATTCATCTGTTTGTATTGACTTCTCATTATTCATGTAG

ACAAAAAGAGACAAATATAGAGAGTTCAAGTGTGTGTGTATGTGTGCAT

AAAGCACTAGATAGGGTTGAGGTTTAGGGCACATCAAACCAATATATAT

ACAACCACTCCTGAATATTCGGTGCAAGTCCACGTACTTTACTTTTTTTT

ACTTTTGAGTTACTCAGGACTCATC  (SEQ ID NO:3)

E14/M60-F-185-P1
GACTGCGTACCAATTCATTACACGACATGTAGATCTAATTGCTGAACAA

AAAAAAAAAAAAAAAGCAATTCTGCAAGAACTCCAGAAACAAAATTAG

GGGTAGGCTTTTTTGTCTATAGAAAAGTAGTTGGTGTGACAGAACCATT

GTTTGCAATAGGCTGGAGTTACTCAGGACTCATC  (SEQ ID NO:4)
```

-continued

E11/M62-F-200-P1
GNCTGCGGACCAATTCAACTGTAAACTAGGAAACTCTAATGATCTAGTTT

TAGTTGATATTGAACAATATCAACGTCTCGTGGGTAAATTGATTTACTTA

TCCCATACTTGTCCTGATATTTCCTTTGCTGTGAGTGTTGTCACCCAGTT

TATGCAGGCTCCTTATGAGAAACACATGGAAGTTACTCAGGACTCATC
(SEQ ID NO:5)

E18/M15-F-221-P2
GACGTACCAATTCCTGCAGATAGATTATGCCGCTTAGAATGTCATGAGT

GACCGAGATGGTAGATTCATTGGCACATTTTGGACTAAACTATTCACTTT

CTCAGGAACAAGTCTGAATGTGTCCTCAAGTTACCATCCTCAAATAGAC

GGTCAGATCGAACGATTCAAATGTATGCTCGAATAATATTTGCGCCATTT

TGTTACTCAGGACTCATC (SEQ ID NO:6)

E13/M17-F-226-P2
GACTGCGTACCAATTCAGAGACGTGGTTTTATAAAAAAGAGAAAAAAG

CTATTAGGGACATAGCTGGCAAATATAAGATGATCAGTCATATTGCTCA

TACTCATAGAGTCATAGCAAGTCTAAGGATTACTTTGAGATTGCTTTATT

TACAAAATGTTGGTTAGAGAGACATCAATTTTTTTAGGAAGCCAATCTCT

AGAACTACGTTACTCAGGACTCATC (SEQ ID NO:7)

E21/M16-F-080-P2
GACTGCGTACCAATTCGGTGGTTAGATTGTATTTCTACAATCTCTTTGTC

GTTGGGTTGGTTACTCAGGACTCATC (SEQ ID NO:8)

Inheritance Studies

To determine the mode of inheritance, the phenotype of the IL was compared to that of a heterozygous IL and a hybrid IL. The results are displayed in Table 2.

TABLE 2

Results of inheritance studies. (IL, original (homozygous) introgression line of the library; F1 IL is the IL crossed with the recurrent parent; HY IL is the IL crossed with the other parental line of the commercial variety (father line)).

| | No. of fruits per block | | Kg fruits per block | |
|---|---|---|---|---|
| | Without introgression | With introgression | Without introgression | With introgression |
| Donor | — | 108 | — | 20 |
| Homozygous introgression segment = IL (LIL 4-1) | 156 | 229 (+47%) | 41 | 54 (+32%) |
| Heterozygous introgression segment = F1 IL (LIL 4-1) | 156 | 187 (+20%) | 41 | 49 (+20%) |
| Hybrid + heterozygous introgression segment = HY IL (LIL 4-1) | 178 | 208 (+17%) | 51 | 61 (+20%) |

Typical additional characteristics of the donor accession are: abundant male flowering, short fruit and high fruit abortion: no commercial value.

The homozygous, heterozygous and hybrid plants do no longer possess these negative traits and have a considerably higher yield which exceeds by far those of a commercial hybrid. The distal parts of the fruit had a distinctive star-shaped yellow colouring, which is believed to be the result of linkage drag. The above-referred negative traits of the donor line have been removed by conventional breeding methods (back crossing).

What is claimed:

1. A plant of a cucumber breeding line having an introgression from cucumber accession PI 169383, a representative sample of seed of which has been deposited with the NCIMB, Aberdeen, Scotland under accession number NCIMB 41532 and depositors reference PI 169383, wherein said introgression is an introgression on linkage group 3 and/or 4 associated with increased yield of said plants, and wherein said plant exhibits an increased yield relative to a plant of said cucumber breeding line lacking said introgression, and said increased yield refers to a higher total fruit weight per plant,
wherein introgression on linkage group 3 and/or 4 comprises:
at least one segment on linkage group 4 selected from the group consisting of:
i) the segment associated with AFLP markers E12/M24-F-063-P2; E11/M62-F-200-P1;
ii) the segment associated with AFLP markers E12/M24-F-177-P2; E12/M24-F-176-P1; E25/M13-F-128-P2;
iii) the segment associated with AFLP marker E21/M16-F-080-P2; and/or a chromosome substitution of linkage group 3.

2. Plant according to claim 1, wherein said plant is a plant of an essentially homozygous pure elite breeding line.

3. Plant according to claim 1, wherein said plant essentially does not have any other introgressions from cucumber accession PI 169383.

4. A cucumber seed produced by crossing or selfing the cucumber plant of claim 1, wherein said seed comprises said introgression on linkage group 3 and/or 4.

5. A cucumber plant produced by growing the seed of claim 4, wherein said seed comprises said introgression on linkage group 3 and/or 4.

6. A plant part of the plant of claim 5.

7. Plant part according to claim 6, wherein the plant part is a cucumber fruit or seed.

8. A method for producing a hybrid cucumber seed comprising crossing the plant according to claim 1 with another cucumber plant and harvesting the resultant hybrid cucumber seed.

9. The method according to claim 8, wherein said other cucumber plant is a plant of an essentially homozygous pure elite breeding line that differs from the breeding line of cucumber according to claim 2.

10. A hybrid cucumber seed produced by the method of claim 8, wherein said hybrid seed comprises said introgression on linkage group 3 and/or 4.

11. A hybrid cucumber plant, produced by growing the hybrid cucumber seed of claim 10, wherein said plant comprises said introgression on linkage group 3 and/or 4.

12. A plant part of the hybrid cucumber plant of claim 11, wherein said plant part comprises said introgression on linkage group 3 and/or 4.

13. A method for improving the yield of a plant of a cucumber breeding line, said method comprising the steps of:
a) crossing a plant of a cucumber breeding line with a plant of cucumber line PI 169383;
b) selecting a progeny cucumber plant resulting from said crossing having an introgression from cucumber accession PI 169383 on linkage group 4 associated with increased yield, wherein said introgression on linkage group 4 is selected from the group consisting of:
i) the segment associated with AFLP markers E12/M24-F-063-P2; E11/M62-F-200-P1;
ii) the segment associated with AFLP markers E12/M24-F-177-P2; E12/M24-F-176-P1; E25/M13-F-128-P2;
iii) the segment associated with AFLP marker E21/M16-F-080-P2;
c) selfing and/or backcrossing said progeny cucumber plant selected in step (b) using said cucumber breeding line as a recurrent parent;
d) selecting a progeny cucumber plant resulting from the selfing or backcrossing in step (c) having an introgression from cucumber accession PI 169383 on linkage group 4 associated with increased yield
e) repeating said steps of selfing and/or backcrossing and selection of steps (c) and (d) to provide a plant of a cucumber breeding line essentially homozygous for said introgression, wherein at least one selection as performed in steps (b) or (d) is performed by marker-assisted selection.

14. Method according to claim 13, wherein said cucumber breeding line is an elite line.

15. A method for improving the yield of an F1 cucumber hybrid, said method comprising the steps of:
  a) crossing a plant of at least a first parental line of said F1 cucumber hybrid with a plant of cucumber line PI 169383;
  b) selecting a progeny cucumber plant resulting from said crossing having an introgression from cucumber accession PI 169383 on linkage group 4 associated with increased yield; wherein said introgression on linkage group 4 is selected from the group consisting of:
    i) the segment associated with AFLP markers E12/M24-F-063-P2; E11/M62-F-200-P1;
    ii) the segment associated with AFLP markers E12/M24-F-177-P2; E12/M24-F-176-P1; E25/M13-F-128-P2;
    iii) the segment associated with AFLP marker E21/M16-F-080-P2;
  c) selfing and/or backcrossing said progeny cucumber plant selected in step (b) using said parental line of said F1 cucumber hybrid as a recurrent parent;
  d) selecting a progeny cucumber plant resulting from the selfing or backcrossing in step (c) having an introgression from cucumber accession PI 169383 on linkage group 4 associated with increased yield
  e) repeating said steps of selfing and/or backcrossing and selection of steps (c) and (d) to provide a parental line of said F1 cucumber hybrid essentially homozygous for said introgression,
  f) using said parental line obtained in step (e) as a parental line for the production of an F1 hybrid having increased yield,
wherein at least one selection as performed in steps (b) or (d) is performed by marker-assisted selection.

16. A cucumber breeding line or an F1 cucumber hybrid obtained by a method according to claim 13 wherein plants of said line comprise said introgression on linkage group 4.

17. A method for detecting a QTL associated with increased yield in cucumber plants comprising the steps of:
  providing an oligonucleotide or polynucleotide capable of hybridizing under stringent hybridization conditions to a AFLP marker,
  contacting said oligonucleotide or polynucleotide with a digested genomic nucleic acid of cucumber plants, and
  determining the presence of specific hybridization of said oligonucleotide or polynucleotide to said digested genomic nucleic acid, wherein said AFLP marker is selected from the group consisting of E12/M24-F-063-P2; E11/M62-F-200-P1; E12/M24-F177-P2; E12/M24-F-176-P1; E25/M13-F-128-P2 and E21/M16-F-080-P2.

18. A method for selecting a cucumber plant or part thereof, including a seed, comprising the steps of:
  (a) providing a progeny cucumber plant or part thereof by crossing a plant of a cucumber breeding line with a plant of cucumber line PI 169383
  (b) testing said progeny cucumber plant or part thereof for the presence of an introgression segment from cucumber accession PI 169383, wherein said introgression is an introgression on linkage group 4 associated with increased yield of said plants wherein said segment is selected from the group consisting of:
    i) the segment associated with AFLP markers E12/M24-F-063-P2; E11/M62-F-200-P1;
    ii) the segment associated with AFLP markers E12/M24-F-177-P2; E12/M24-F-176P1; E25/M13-F-128-P2;
    iii) the segment associated with AFLP marker E21/M16-F-080-P2; and/or
  a chromosome substitution of linkage group 3,
  (c) selecting said progeny cucumber plant or part thereof based on the information derived from said testing; and
  (d) optionally using said information for further breeding considerations.

\* \* \* \* \*

UNITED STATES PATENT AND TRADEMARK OFFICE
CERTIFICATE OF CORRECTION

PATENT NO.        : 8,878,012 B2                          Page 1 of 1
APPLICATION NO.   : 12/794863
DATED             : November 4, 2014
INVENTOR(S)       : Anita Afke de Haan et al.

It is certified that error appears in the above-identified patent and that said Letters Patent is hereby corrected as shown below:

Title Page, Item (75), please delete "Bleiswiji" and insert --Bleiswijk--

Title Page, Item (30), please delete "07150267" and insert --07150267.8--

In the Claims,

Column 31, Line 55, please delete "selling" and insert --selfing--

Signed and Sealed this
Seventeenth Day of March, 2015

Michelle K. Lee
*Director of the United States Patent and Trademark Office*